United States Patent
Lane-Smith

[11] Patent Number: 6,018,985
[45] Date of Patent: Feb. 1, 2000

[54] METHOD AND APPARATUS FOR MEASURING UNATTACHED RADON PROGENY

[75] Inventor: Derek Lane-Smith, Billerica, Mass.

[73] Assignee: Durridge Co., Bedford, Mass.

[21] Appl. No.: 09/019,713

[22] Filed: Feb. 6, 1998

[51] Int. Cl.[7] .................................................. G01N 27/04
[52] U.S. Cl. ...................... 73/28.02; 73/31.02; 250/282; 250/DIG. 2; 324/693
[58] Field of Search ................. 73/28.02, 28.01, 73/31.02; 280/281, 282, DIG. 2, 253, 255; 454/909; 324/693

[56] References Cited

U.S. PATENT DOCUMENTS

| | | | |
|---|---|---|---|
| 4,451,736 | 5/1984 | Cameron | 250/376 |
| 4,847,503 | 7/1989 | Tetley et al. | 250/435 |
| 4,868,386 | 9/1989 | Ilmasti | 250/253 |
| 4,977,318 | 12/1990 | Ilmasti et al. | 250/253 |
| 5,514,872 | 5/1996 | Bolton et al. | 250/380 |
| 5,834,628 | 11/1998 | Hunter et al. | 73/28.04 |

*Primary Examiner*—Michael Brock
*Attorney, Agent, or Firm*—Dinesh Agrawal, P.C.

[57] ABSTRACT

A method and apparatus for measuring the concentration of unattached Radon progeny in air is described. The method consists of measuring the conductivity of the air or alternatively the concentration of fast ions in the air, and converting the measurement to a concentration of unattached Radon progeny by applying a predetermined ratio found to exist between conductivity and the concentration of unattached Radon progeny on the one hand, or between the concentrations of fast ions and unattached Radon progeny on the other hand. Apparatus for implementing the method includes means for measuring conductivity (or fast ion concentration), means for calculating the concentration of unattached Radon progeny using the predetermined ratios and output means for displaying the result of the calculation.

8 Claims, 2 Drawing Sheets

METHOD AND APPARATUS FOR MEASURING UNATTACHED RADON PROGENY

FIELD OF THE INVENTION

This invention relates to a method and apparatus for measuring the concentration of unattached Radon progeny in air.

BACKGROUND OF THE INVENTION

Radon 222 and its isotope Radon 220 (Thoron) are radioactive, chemically inert gasses which occur in the natural radioactive decay chains of Uranium and Thorium. As gasses they are able to diffuse out of the soil or concrete where they are formed and collect in spaces where people live and work.

The progeny of Radon are metals such as Polonium, Bismuth and Lead which are also radioactive. When breathed in, they tend to stick in the throat or lungs. Subsequent radioactive decays occur on the tissue surface and bombards the tissue with high-energy alpha and beta particles, causing damage to the cells. The radiation damage caused by these radon progeny can result in cancer.

When a Radon atom decays, it emits an alpha particle with an energy of several million electron volts. The alpha particle ionizes a path in the air several centimeters long, creating several hundred thousand pairs of positive atoms and negative electrons. The Polonium daughter of the Radon recoils from the decay and itself becomes positively ionized. Within a millisecond, in normal humidity, those positive atoms and negative electrons which have not recombined with each other will have acquired several water molecules to form a cluster molecule around the single charge. These charged cluster molecules are stable and have a lifetime in clean, free air of several minutes. Atmospheric electricians refer to such cluster molecules as "Fast Ions". The cluster molecule containing the radioactive Polonium atom is called an "unattached daughter".

The fast ions are responsive to electric fields, including those created between the ion and its image in a surface or in a large particle. They are thus sticky and are quickly swept out of the air if there are particles suspended in the air or if the walls are close. When a fast ion is captured by a dust particle or "Aitken Nucleus", it becomes a "slow ion" as it is no longer mobile in an electric field. If the cluster molecule around the Polonium daughter is captured by a heavy particle it becomes "attached".

Most radiation-damaged cells either die or are repaired satisfactorily. A very few, however, may be damaged in such a way as to promote unlimited reproduction causing cancer. Lung tissue is most sensitive to is kind of damage. It is recognized that exposure to radiation from Radon and its progeny is the second biggest cause of lung cancer, after smoking. It is also the biggest cause of death from the built environment.

Typical results show radon levels in outside air over land of 1 to 50 Bq/m$^3$ and indoors anything from outside levels to 1,000 Bq/m$^3$ or more. Extended exposure to levels in excess of 200 Bq/m$^3$ (UK and Hong Kong) or 150 Bq/m$^3$ (USA) are considered dangerous and require mitigation.

Most Radon-induced lung cancer occurs in the bronchial region rather than deeper in the lungs. This is because the unattached radon progeny are readily deposited on the bronchial wall whereas the heavier, attached daughters are carried on their particles by the air flow deeper into the lungs where mechanisms exist to remove them. Thus it is that unattached daughters have more than fifty times the deposition rate of attached daughters and therefore more than fifty times the radiation dose efficiency, as noted in *Radon versus Rn Daughters,* Hans Vanmarcke and Paul Berkvens, *Health Physics,* vol. 56 #2, pp. 229–231, 1989.

Because of the variation of deposition rate between unattached and attached progeny, it transpires that the "working level", or the total concentration of Radon daughters is not an accurate measure of the health risk in a given environment and that the Radon concentration is probably a more useful indicator. This is one reason why the United States Environmental Protection Agency expresses its recommendations in terms of Radon concentrations rather than of concentrations of Radon daughters.

The two major techniques for measuring Radon are:
a) passive, by collection on some absorbing material such as activated carbon, and subsequent analysis, and
b) active, by some sensor and electronic device such as the NITON RAD7 (trademark) electronic Radon detector.

These methods measure just the concentration of the Radon gas and not the daughters.

Instruments are available for measuring the "Working Level" by determining the total concentrations of Radon Progeny. Typically, air is drawn through a filter and the alpha radiation from the filter is measured. Some of the more sophisticated instruments will analyze the spectrum of the alpha energy thus determining the distribution of different daughters on the filter, giving additional information including, for instance, the contribution to the radioactivity from Thoron daughters. These instruments do not distinguish between the attached and unattached fractions of the progeny, collecting both indiscriminately.

A prior art method of measuring the unattached fraction involves collecting the progeny in such a way that attached daughters escape collection, leaving only the previously unattached daughters, and then measuring the alpha radiation from the collected progeny. The standard technique is to use a screen with a mesh big enough to allow nearly all the heavier particles to pass through unimpeded while collecting the small, more mobile unattached daughters on the screen as described in *Unattached fraction of short-lived Rn decay products in indoor and outdoor environments: an improved singe-screen method and results,* A. Reineking and J. Porstendorfer, *Health Physics,* Vol. 58 #6, pp. 715–727, 1990. Other methods have taken advantage of the positive charge on the majority of the unattached daughters to drive them by means of an electric field to a collecting plate or screen where their radioactivity is measured, but this technique is not popular because the uncharged daughters are not collected as discussed in *An evaluation of unattached Radon (and Thoron) daughter measurement techniques,* A. W. Van der Vooren, A. Busigin and C. R. Phillips, *Health Physics,* Vol. 42, pp. 801–808, June 1982. A combination of the screen or 'diffusion battery' to collect the unattached progeny, and a filter to collect the rest provides a means to collect and measure both attached and unattached progeny fractions at once as disclosed in U.S. Pat. No. 4,847,503 to Tetley, W. C. et al., Jul. 11, 1986.

SUMMARY OF THE INVENTION

In its broadest aspect, the invention consists of a method of measuring the concentration of unattached Radon progeny in air by measuring the conductivity of the air or the total concentration of fast ions in the air.

As will be shown, the concentration of unattached Radon progeny can be deduced by applying a predetermined proportionality ratio, which is approximately $10^{15}$ Bq/m$^3$ per $\Omega$m−1, wherein "$\Omega$" represents resistivity.

In one aspect of apparatus according to the invention, there is provided means for measuring the conductivity of air and output means for displaying the measured conductivity. In another of its aspects the invention comprises apparatus including means for measuring the conductivity of air, processing means for calculating the concentration of unattached Radon progeny based on a predetermined relationship between conductivity and such concentration and output means for displaying the calculated concentration.

In yet another aspect of apparatus according to the invention, there is provided means for measuring the concentration of fast ions in air, processing means for calculating the concentration of unattached Radon progeny based on a predetermined relationship with the concentration of fast ions and output means for displaying the calculated concentration.

DETAILED DESCRIPTION OF THE INVENTION

The invention will now be described in detail by reference to the drawings of a preferred embodiment of the apparatus of the invention, in which.

Figure 1:
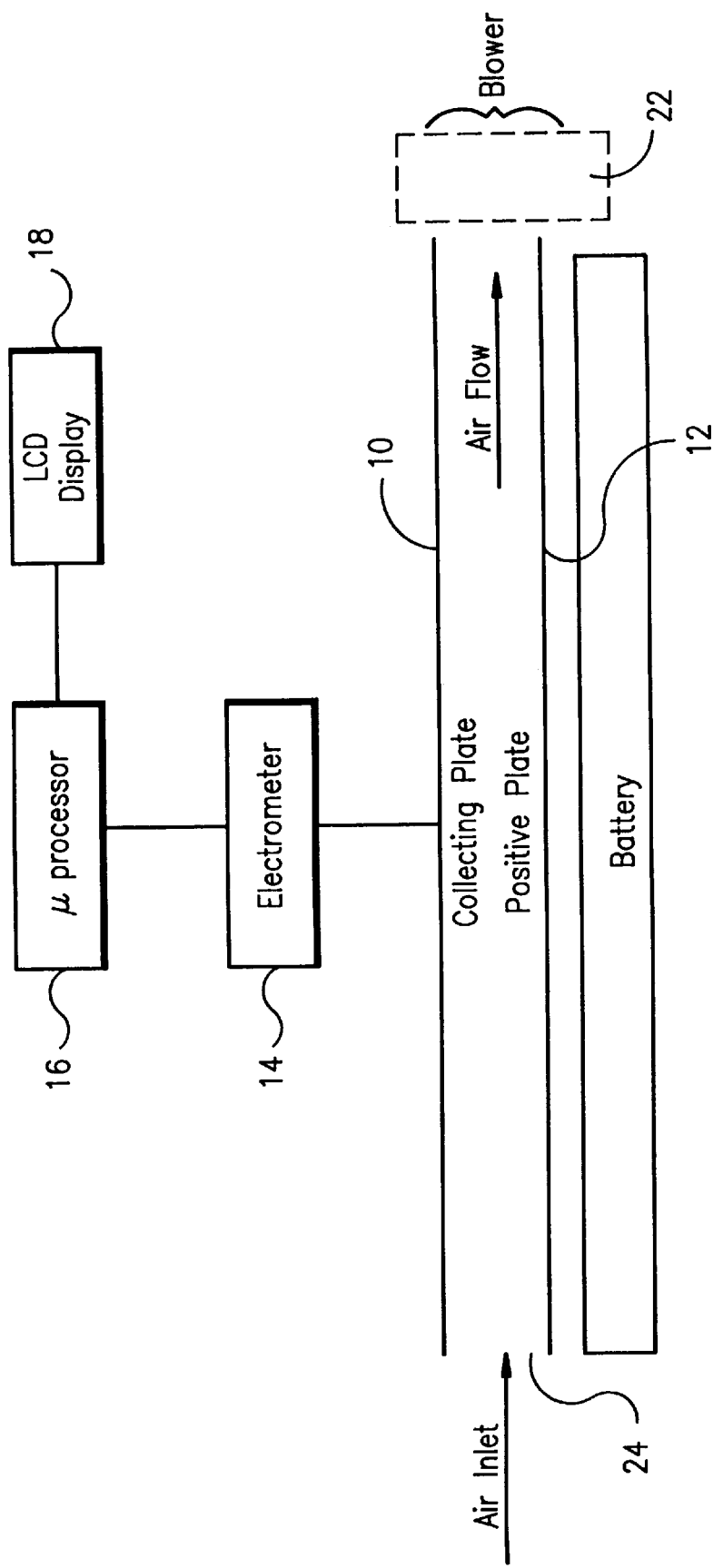
FIG. 1 is a schematic illustration of the operative components of a portable flat Gerdien condenser for measuring the concentration of unattached Radon progeny in air according to the invention.

In normal fair weather there is a vertical potential gradient outdoors at ground level of the order of 100 V/m. At around 20 km above ground the potential is typically around 200,000 V relative to the earth. This "equipotential layer" is fed by thunderstorms and discharged by a current flowing to earth through the air wherever there is fair weather.

The air is not a perfect insulator bat, because of the presence of "fast ions", will carry an electric current in the presence of an electric field. Heavier charged particles contribute little to the conductivity of the air. Other, non-ohmic currents may also flow due, for instance, to the turbulent diffusion of charge gradients. Standard techniques exist for measuring the potential gradient, air-earth current and the conductivity of the air due to both the positive and negative fast ions.

In the upper atmosphere air molecules are ionized mainly by cosmic rays. Closer to the ground however, and indoors, the ionization is produced mainly by the radioactive decay of Radon (and Thoron) and their progeny.

The following are typical parameter values in the lower atmosphere. The conductivity of the outside air is typically of the order of $10^{-14}$ $(\Omega m)^{-1}$. The mobility of positive fast ions is $1.4 \times 10^{-4}$ m$^2$/Vs. This is two to four orders of magnitude more mobile than "slow" or "attached" ions. Fast ion production rate is of the order of $10^7$ m$^{-3}$ s$^{-1}$. Fast ion density in typical air is of the order of $10^9$ m$^{-3}$. The charge on a fast ion is $1.6 \times 10^{-19}$ C.

At ground level and inside buildings virtually all the airborne ions are the result of radioactive decay of Radon, Thoron and their progeny. A very small proportion contain radioactive progeny and the rest are cluster molecules around negative or positives non-radioactive molecules. A Radon level of just a few Bq/m$^3$, which is creating unattached radon daughters at the rate of around 10 m$^{-3}$ s$^{-1}$, produces fast ions at a rate of $10^7$ m$^{-3}$ s$^{-1}$. Therefore, for every unattached daughter created there are the order of one million fast ions produced. There is no preference between radioactive and non-radioactive molecules in terms of any attachment processes. Therefore the ratio of fast ions to radioactive unattached progeny remains constant through all processes of equilibration, transient changes in supply of Radon and/or Thoron or changes in dust burden in the air. From the standard values quoted above it will be appreciated that this ratio is therefore of the order of one million to one.

Similar in some ways to a photomultiplier, the charge created on the atom of a Radon daughter from the recoil of the radioactive decay is, in effect, multiplied by about one million in the ionization produced along the trail of the alpha particle created in the decay process. The total ionization rate occurring in typical ambient Radon concentrations causes a conductivity in the air which is therefore readily measurable.

It also follows from the above that the concentration of fast ions and hence the conductivity of the air indoors or outside in the lower atmosphere is an analogue of the concentration of unattached progeny of Radon and its isotopes. The method of this invention involves measuring the concentration of unattached Radon progeny in air by measuring the conductivity of the air or the concentration of fast ions. For example, a conductivity of the order of $10^{-14}$ $(\Omega m)^{-1}$ corresponds to a typical unattached progeny concentration of the order of 10 Bq/m$^3$ so that the multiplying factor to convert conductivity of air (indoors or in the lower atmosphere) to unattached Radon progeny concentration is of the order of $10^{15}$ Bq/m$^3$ per $(\Omega m)^{-1}$.

It should be noted that it is possible to have other, man-made ionizing processes, such as radioactive static dischargers or electrostatic cleaners, and in these circumstances the conductivity may be greater than that due to the Radon progeny concentration alone and measurements should be interpreted accordingly. In any case, the error, if one exists, will only be to increase the reading.

The accuracy of the method of the invention also depends on a constant ratio of fast ion concentration to unattached radon progeny. In some exceptional circumstances it is possible to remove many fast ions of one sign and have unbalanced conductivity. By measuring only the conductivity due to positive fast ions, the same sign as the unattached progeny, we are able to maintain the constant ratio of conductivity reading to radon progeny as required.

Apparatus for measuring the conductivity of the air and hence the concentration of unattached Radon progeny may include Gerdien Tubes or a "flat Gerdien Condenser".

The classic instrument for measuring the conductivity of air due to ions of both signs consists of two pair of concentric tubes within a grounded box (Gerdien Tubes). The outer cylinder of each pair is raised to an elevated potential; one positive, one negative. Air is blown through both pairs and the electric current airing on the inner electrode of each pair is measured. The concentric pair with a negative outer cylinder drives negative ions to the inner electrode which therefore is measuring negative conductivity. The other tube measures positive conductivity.

The response of the tubes is ohmic, that is the current is proportional to the applied potential, for applied potentials below a saturation level. Above the saturation level all the fast ions are swept out of the air and deposited on the collecting electrode (the inner cylinder). The saturating potential depends on the geometry of the tubes and the speed of the air flow through the tubes. Providing the air flow is fast enough so that the current is not saturated, the current is independent of the air flow velocity and is a true measure of the conductivity of the air. The bigger the tubes and the faster the air flow, the higher can be the applied potential without saturating the tubes and the larger the current signal to be measured, for a given value of the conductivity.

With a conductivity of order $10^{-14}$ $(\Omega m)^{-1}$, the currents being measured are typically of the order of $10^{-3}$ A. Or, if the fast ion concentration is $10^9$ $m^{-3}$ and each carries a charge of $1.6 \times 10^{-19}$ C, then the fast ions in one liter of air cry a total of $1.6 \times 10^{-13}$ C and the maximum current that can be drawn from a stream of air is $1.6 \times 10^{-13}$ L amperes, where L is the air flow in liters per second. Electrometer techniques are necessary to measure such small currents. All insulation must be as good as air. Outstanding insulating materials, such as PTFE, are used in the construction and care is taken to ensure that leakage takes place only over long, clean and dry leakage paths. In regions of significant Radon concentration the conductivity of the air will be 10 to 1,000 times higher than the values quoted here.

Figure 2:
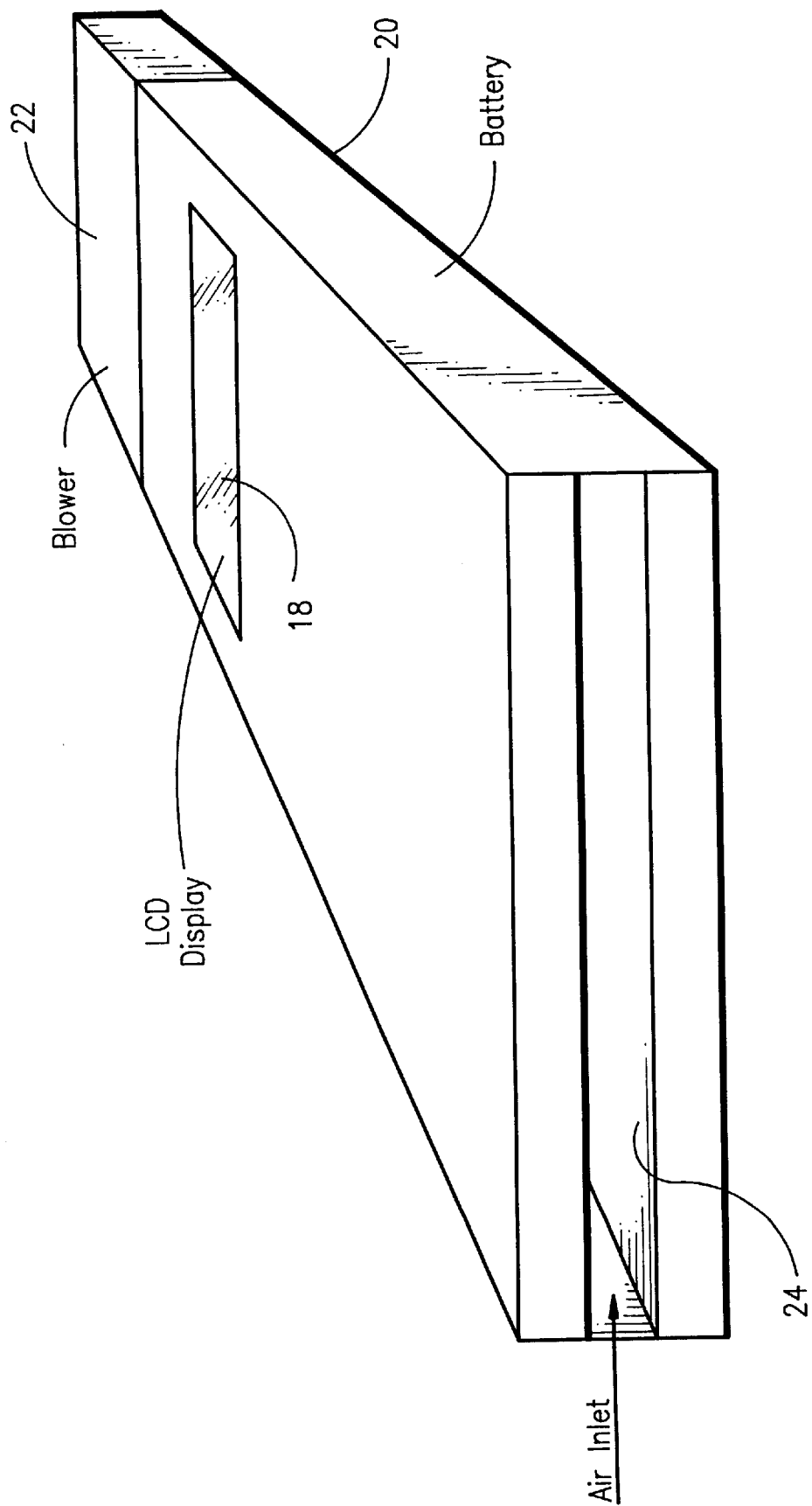
FIG. 2 is a perspective view of an assembly containing the components of FIG. 1.

A more convenient design of Gerdien condenser is illustrated in FIGS. 1 and 2 and consists of two parallel plates 10, 12 inside a grounded box 20. An air blower 22 pulls air into air inlet 24 and through the instrument between the plates 10, 12. One plate is held at an elevated potential (below saturation) while the other is connected to an electrometer 14 to measure the current. If V is the applied potential, d is the distance between the plates, A is the area of the plates and I is the measured current, then the conductivity, YId/VA. The availability today of very high performance solid-state electrometer chips makes the design and manufacture of such portable unattached Radon progeny meters feasible. Techniques known to those skilled in the art are incorporated in the circuitry associated with the condenser to reduce electrical noise and eliminate offsets. If the elevated plate potential is above saturation and the air flow rate is measured, the instrument is measuring the total fast ion concentration. If the measured current is I ampere, the flow velocity is U $m^3 s^{-1}$ and q is the charge on an ion ($1.6 \times 10^{-19}$ C), then the fast ion concentration, N $m^{-3}$, is given by $N = I/qU = 6.25 \times 10^{18}$ I/U.

The current or fast ion concentration measured by electrometer 14 is indicated to microprocessor 16, which calculates the conductivity (or fast ion concentration) and performs the conversion to concentration of unattached Radon progeny as described above. The measured concentration is outputted to LCD display 18. A battery 21 is provided to operate the electrometer 14, microprocessor 16 and blower 22.

It will be appreciated that the preferred embodiments of the invention have been described but that variations may be practised without departing from the scope of the invention.

What is claimed is:

1. In an air sample including attached and unattached Radon progeny, a method of measuring the concentration of the unattached Radon progeny, comprising the steps of:
    a) providing an air sample including attached and unattached Radon progeny;
    b) measuring the conductivity of the air sample;
    c) applying a predetermined ratio of proportionality to the measured conductivity to obtain a value representing the concentration of the unattached Radon progeny in the air sample.

2. The method of claim 1, wherein:
    said ratio of proportionality is approximately $10^{15}$ Bq/m$^3$ per $(\Omega m)^{-1}$.

3. In an air sample including attached and unattached Radon progeny, a method of measuring the concentration of the unattached Radon progeny, comprising the steps of:
    a) providing an air sample including attached and unattached Radon progeny;
    b) measuring the concentration of fast ions in the air sample;
    c) applying a predetermined ratio of proportionality to the measured concentration of fast ions to obtain a value representing the concentration of the unattached Radon progeny in the air sample.

4. The method of claim 3, wherein:
    said ratio of proportionality is approximately $10^{-8}$ Bq/m$^3$ per m$^{-3}$.

5. An apparatus for measuring the concentration of unattached Radon progeny in an air sample, comprising:
    a) means for measuring the conductivity of an air sample;
    b) processing means operably associated with said conductivity measuring means for calculating the concentration of the unattached Radon progeny based on a predetermined ratio of proportionality; and
    c) means for displaying the results of said processing means.

6. The apparatus of claim 5, wherein:
    a) said predetermined ratio of proportionality is approximately $10^{15}$ Bq/m$^3$ per $(\Omega m)^{-1}$.

7. An apparatus for measuring the concentration of unattached Radon progeny in an air sample, comprising:
    a) means for measuring the concentration of fast ions in an air sample;
    b) processing means operably associated with said fast ion concentration measuring means for calculating the concentration of the unattached Radon progeny based on a predetermined ratio of proportionality; and
    c) means for displaying the results of said processing means.

8. The apparatus of claim 7, wherein:
    a) said predetermined ratio of proportionality is approximately $10^{-8}$ Bq/m$^3$ per m$^{-3}$.

* * * * *